United States Patent
Hwang

(10) Patent No.: US 12,427,276 B2
(45) Date of Patent: Sep. 30, 2025

(54) MEDICAL SYSTEM WITH SEPARATOR DEVICE

(71) Applicant: CANON U.S.A., INC., Melville, NY (US)

(72) Inventor: Charles George Hwang, Wellesley, MA (US)

(73) Assignee: Canon U.S.A., Inc., Melville, NY (US)

( * ) Notice: Subject to any disclaimer, the term of this patent is extended or adjusted under 35 U.S.C. 154(b) by 1145 days.

(21) Appl. No.: 17/232,783

(22) Filed: Apr. 16, 2021

(65) Prior Publication Data

US 2022/0331534 A1    Oct. 20, 2022

(51) Int. Cl.
| | |
|---|---|
| *A61M 16/04* | (2006.01) |
| *A61B 34/20* | (2016.01) |
| *A61B 34/30* | (2016.01) |
| *A61M 16/08* | (2006.01) |
| *A61M 25/00* | (2006.01) |

(52) U.S. Cl.
CPC .............. *A61M 16/04* (2013.01); *A61B 34/20* (2016.02); *A61M 16/0463* (2013.01); *A61M 16/0816* (2013.01); *A61M 25/0013* (2013.01); *A61B 2034/301* (2016.02)

(58) Field of Classification Search
CPC .............. A61M 16/04; A61M 16/0463; A61M 16/0816; A61M 25/0113
See application file for complete search history.

(56) References Cited

U.S. PATENT DOCUMENTS

| | | | | |
|---|---|---|---|---|
| 6,109,259 | A | * | 8/2000 | Fitzgerald ......... A61M 16/0833 128/207.14 |
| 9,737,371 | B2 | | 8/2017 | Romo et al. |
| 2014/0150782 | A1 | * | 6/2014 | Vazales ............. A61M 25/1018 128/202.16 |
| 2017/0007792 | A1 | * | 1/2017 | Nye ................... A61M 16/0816 |

(Continued)

FOREIGN PATENT DOCUMENTS

| | | |
|---|---|---|
| WO | 2018/204202 A1 | 11/2018 |
| WO | WO-2020014201 A1 * | 1/2020 ......... A61B 1/00057 |

(Continued)

OTHER PUBLICATIONS

How Ion Works, Intuitive/Robotic Assisted Bronchoscopy, https://www.intuitive.com/en-us/products-and-services/ion/how-ion-works, retrieved May 10, 2021.

*Primary Examiner* — Erin McGrath
(74) *Attorney, Agent, or Firm* — Canon U.S.A., Inc. I.P. Division

(57) ABSTRACT

A medical system comprises an operation console, a support platform configured to support a catheter, a driving unit moveably coupled to the support platform, the driving unit being configured to advance or retract the catheter based on an instruction from the operation console, a support platform configured to support a catheter, a separator device including: a first end, a second end opposite the first end, and a fixed length portion between the first end and the second end, and a medical tube adaptor including: a first end, and a second end opposite the first end and mateable with a medical tube. The medical tube is insertable into a mouth of a patient. The second end of the separator device is mateable with or attached to the first end of the medical tube adapter.

21 Claims, 10 Drawing Sheets

(56) References Cited

U.S. PATENT DOCUMENTS

| | | |
|---|---|---|
| 2018/0243900 A1 | 8/2018 | Tanaka et al. |
| 2018/0311006 A1 | 11/2018 | Kose et al. |
| 2019/0015978 A1 | 1/2019 | Takagi et al. |
| 2019/0038860 A1* | 2/2019 | Lykins .................. A61M 16/04 |
| 2019/0105468 A1 | 4/2019 | Kato et al. |
| 2019/0269368 A1* | 9/2019 | Hauck .................... A61B 34/71 |

FOREIGN PATENT DOCUMENTS

| | | |
|---|---|---|
| WO | 2020/086749 A1 | 4/2020 |
| WO | 2020/092096 A2 | 5/2020 |

\* cited by examiner

MEDICAL SYSTEM WITH SEPARATOR DEVICE

FIELD OF DISCLOSURE

The present disclosure relates generally to systems and methods for medical applications. More particularly, the subject disclosure is directed to a system using an articulated medical device, wherein the medical device is capable of maneuvering within a patient.

BACKGROUND OF THE DISCLOSURE

Bendable medical devices such as endoscopic surgical devices and catheters are well known and continue to gain acceptance in the medical field. The bendable medical device generally includes a flexible body commonly referred to as a sleeves or sheaths. One or more tool channels extend along (typically inside) the flexible body to allow access to a target located at a distal end of the body.

The medical device is intended to provide flexible access within a patient, with at least one curve or more leading to the intended target, while retaining torsional and longitudinal rigidity so that a physician can control the tool located at the distal end of the medical device by maneuvering the proximal end of the device.

The medical device may be implemented via a system, where the system includes both hardware and software that when used together allow the user to guide and observe the movement of the medical device through passageways within a patient. By way of example, United States patent publication number 2019/0105468, describes such a system for implementing an articulated medical device having a hollow cavity, where the device is capable of maneuvering within a patient, and allowing a medical tool to be guided through the hollow cavity for medical procedures, including endoscopes, cameras, and catheters. When navigating the articulated medical device to a target location within the body with navigation software and robotic assistance, it is necessary for the system to know the relative starting position of the medical device. However, the starting position of the medical device may vary depending on where the operator positions the support platform holding the medical device relative to the patient's mouth. In order to account for the potential different locations, some systems may use encoding/tracking systems, which are complex, physically large, and costly.

Accordingly, there exists a need in the art for a medical system that resolves the issue different relative starting positions of the medical device without being complex, large, and/or costly.

SUMMARY

The subject disclosure provides a medical system comprising an operation console, a support platform configured to support a catheter, a driving unit moveably coupled to the support platform, the driving unit being configured to advance or retract the catheter based on an instruction from the operation console, a support platform configured to support the catheter, a separator device including: a first end, a second end opposite the first end, and a fixed length portion between the first end and the second end, and a medical tube adaptor including: a first end, and a second end opposite the first end and mateable with a medical tube. The medical tube is insertable into a mouth of a patient. The second end of the separator device is mateable with or attached to the first end of the medical tube adapter.

The subject disclosure also provides a method of performing a medical procedure using a medical system. The medical system includes an operation console, a support platform configured to support a catheter, a driving unit moveably coupled to the support platform, the driving unit being configured to advance or retract the catheter based on an instruction from the operation console, a support platform configured to support the catheter; a separator device including: a first end; a second end opposite the first end; and a fixed length portion between the first end and the second end; and a medical tube adaptor including: a first end; and a second end opposite the first end and mated with a medical tube. The medical tube is insertable into a mouth of a patient. The method comprises a) coupling the first end of the separator device to the support platform; and mating the second end of the separator device with the first end of the medical tube adapter; or b) aligning the first end of the separator device with an alignment indicator of separator device, wherein the second end of the separator device is attached to the first end of the medical tube adapter; and c) actuating the driving unit to advance the catheter into the medical tube via the medical tube adapter.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
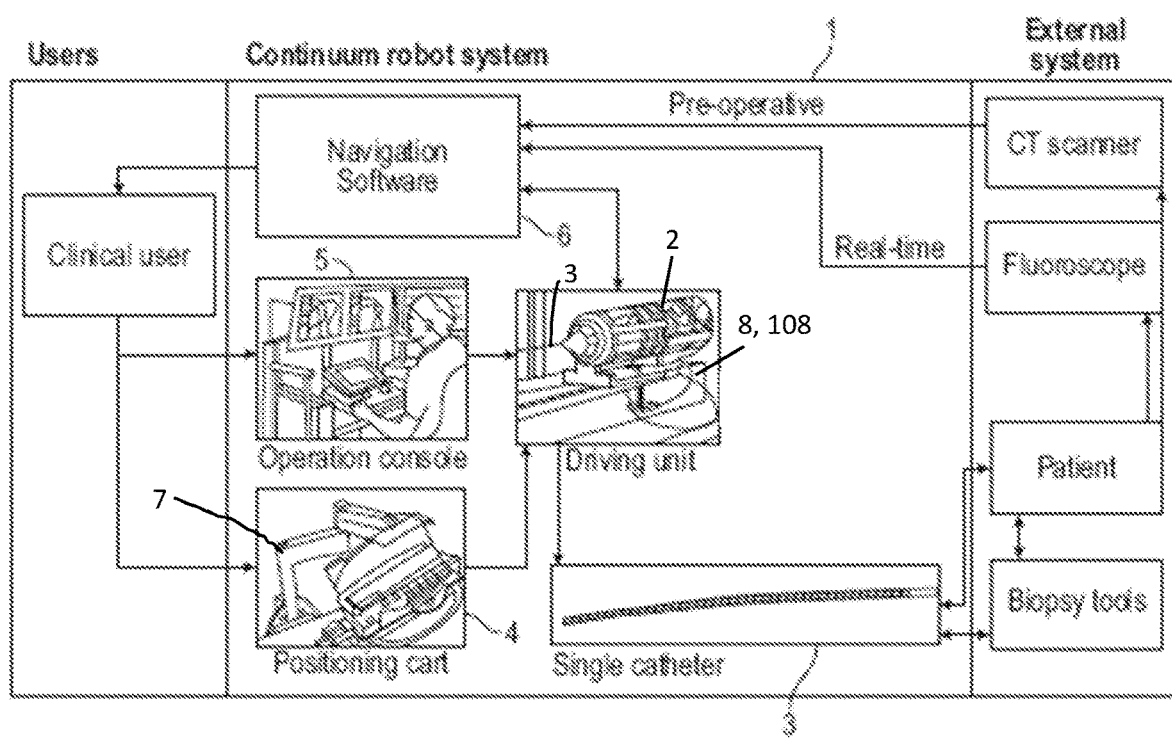
FIG. 1 illustrates an example embodiment of a system to allow a user to guide and observe the movement of a medical device within a patient.

Throughout the Figures, the same reference numerals and characters, unless otherwise stated, are used to denote like features, elements, components or portions of the illustrated embodiments. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

FIG. 1 illustrates an example embodiment of a medical system 1. The medical system 1 (also referred herein as a continuum robot system) comprises a driving unit 2, a bendable medical device 3 (or sheath or catheter), a positioning cart 4, an operation console 5, and navigation software 6. The positioning cart 4 and the operation console 5 may be formed as a single structure. That is, the operation console 5 may be attached to and carried by the positioning cart 4. The system 1 also interacts with clinical users and external systems (e.g., a computerized tomography (CT) scanner and/or magnetic resonance imaging (MRI) scanner, a fluoroscope, a patient, biopsy tools).

The navigation software 6 and the driving unit 2 are communicatively coupled via a bus, which transmits data between them. Moreover, the navigation software 6 is coupled to and communicates with a CT scanner or MRI scanner, a fluoroscope, and an image server (not in FIG. 1), which are external of the medical system 1. The image server may be, for example, a DISCOM server that is coupled to a medical imaging device, such as a CT scanner, a MRI scanner, and a fluoroscope. The navigation software 6 processes data provided by the driving unit 2, data provided by images stored on the image server, images from the CT scanner/MRI scanner, and images from the fluoroscope in order to display images on a display device.

The images from the CT scanner/MRI scanner are pre-operatively provided to the navigation software 6. With the navigation software 6, a clinical user can create an anatomical computer model from the images. In some embodiments, the anatomy is lung airways. From the chest images of the CT scanner/MRI scanner, the clinical user can segment the lung airways for clinical treatments, such as a biopsy.

After generating the lung-airway map, the clinical user can also create a plan to access the lesion for a biopsy. The plan includes the airways to insert the medical device 3 and the lesion.

The driving unit 2 comprises actuators and a control circuitry. The control circuitry is communicatively-coupled with the operation console 5. Also, the driving unit 2 is connected to the medical device 3 so that the actuators in the driving unit 2 operate the medical device 3. Therefore, a clinical user can control the medical device 3 via the driving unit 2.

The driving unit 2 is physically connected to a positioning cart 4. The positioning cart 4 includes a positioning arm 7 and a support platform 8, 108, and the positioning cart 4 locates the driving unit 2 and the medical device 3 in the intended position near a patient. More particularly, the driving unit 2 is moveably mounted to the support platform 8, 108, with the support platform 8, 108 being connected to the positioning arm 7 and being positionable via the positioning arm 7. The medical system 1 includes a separator device 10, 100 that can be used to assist in positioning support platform 8, 108 at a predetermined distance from the patient, which is discussed below. The clinical user can insert and retreat the medical device 3 to perform a biopsy in the airways of the patient once the support platform 8, 108 and driving unit 2 are in the proper position.

The medical device 3 can be navigated to the lesion in the airways based on the plan by the clinical user's operation. The medical device 3 includes a tool channel for a biopsy tool. The medical device 3 can guide the biopsy tool to the lesion of the patient. The clinical user can take a biopsy sample from the lesion with the biopsy tool.

An example of a bendable medical device and a method of using the medical device via the medical system 1 is described in United States Pat. Pub. No. 2019/0105468, which is incorporated by reference herein in its entirety. Other examples of bendable medical devices and methods of using the medical device via the medical system are disclosed in United States Pat. Pub. Nos. 2018/0243900; 2018/0311006; 2019/0105468; and 2019/0015978; and PCT Pub. Nos. WO2018/204202; WO/2020/086749; and WO/2020/092096, all of which are incorporated by reference herein in their entirety.

Figure 2:
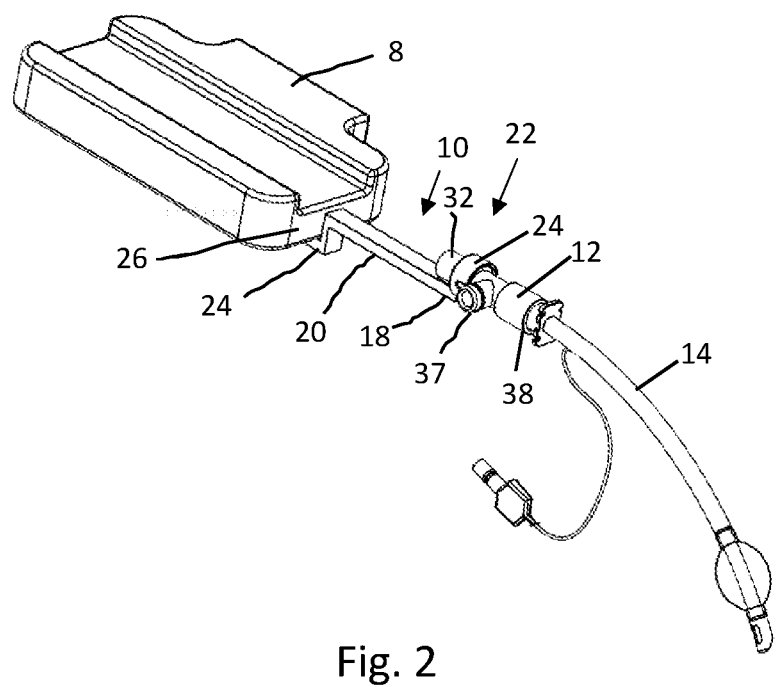
FIG. 2 shows a perspective view of a portion of the system of FIG. 1, where a support platform, a separator device, a medical tube adapter, and a medical tube are shown, in accordance with a first example embodiment.
Figure 3:
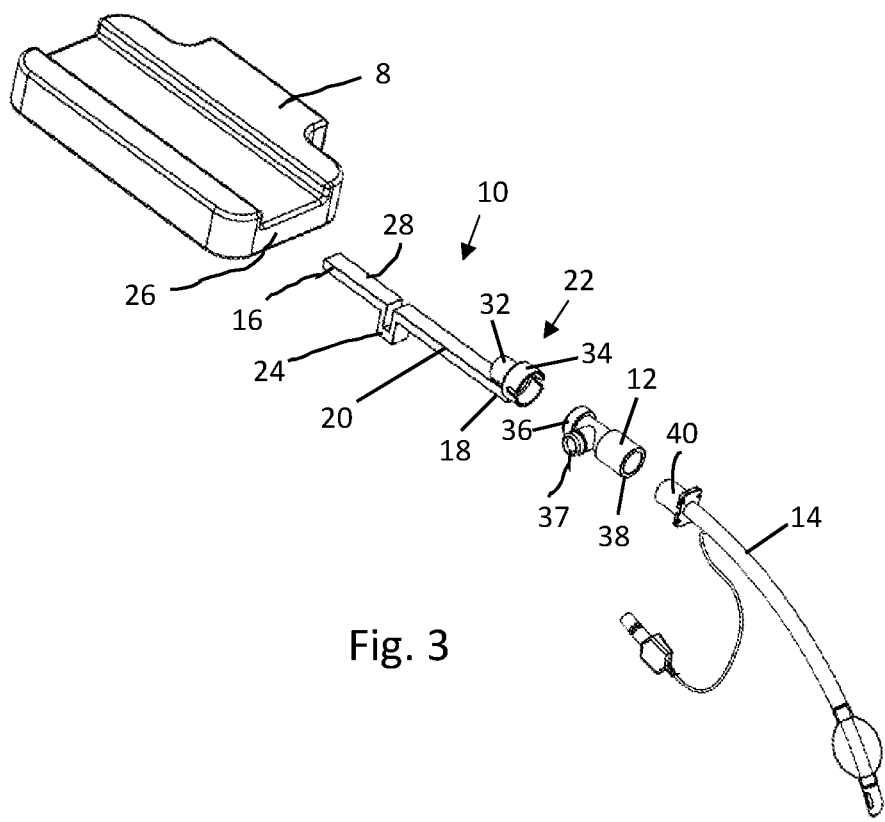
FIG. 3 shows an exploded perspective view of first example embodiment of FIG. 2.
Figure 4:
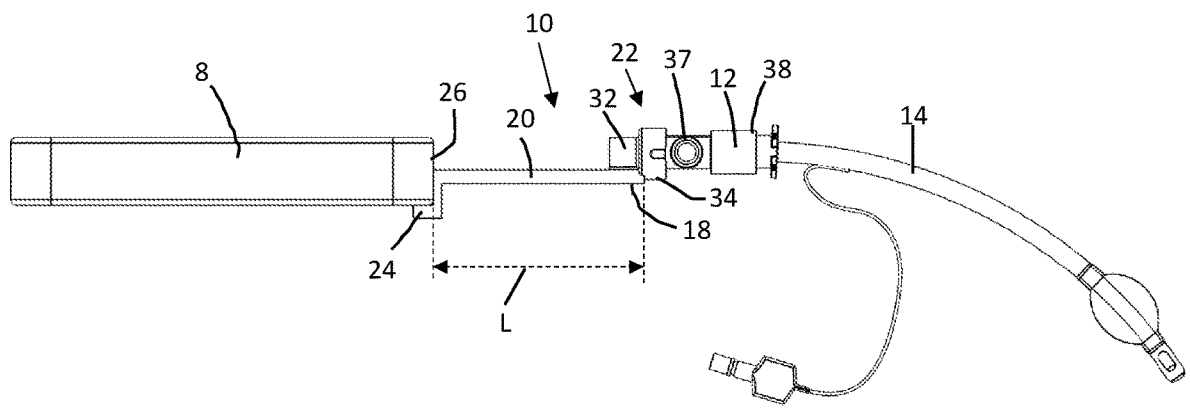
FIG. 4 shows a side view of the first example embodiment of FIG. 2.
Figure 5:
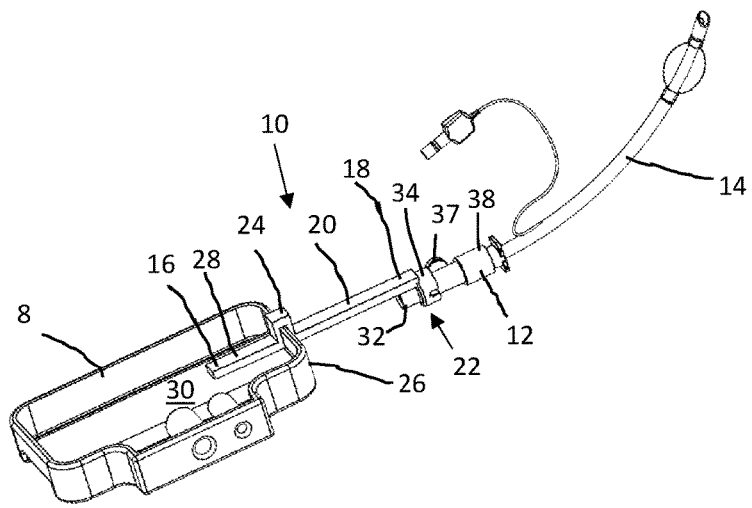
FIG. 5 shows an underside perspective view of first example embodiment of FIG. 2.

FIG. 2 shows a perspective view of a portion of the medical system 1 in accordance with a first example embodiment, where a support platform 8, a separator device 10, a medical tube adapter 12, and a medical tube 14 are shown. The medical tube 14 may be an endotracheal tube, for example, or any medical tube that is inserted into the mouth of a patient. In the case of the medical tube 14 being an endotracheal tube, the medical tube adapter 12 may be referred to as endotracheal tube adapter. Another example of a medical tube is a laryngeal mask airway. FIG. 3 shows an exploded perspective view of first example embodiment of FIG. 2. FIG. 4 shows a side view of first example embodiment of FIG. 2. FIG. 5 shows an underside perspective view of first example embodiment of FIG. 2.

The support platform 8 is configured to support the driving unit 2, which advances the medical device 3 during a medical procedure. In particular, the support platform 8 may include rails, where the driving unit is movable along the rails to advance or retract the medical device 3 during the medical procedure. The driving unit 2 and the medical device 3 are not shown in FIGS. 2-12.

As shown in FIGS. 2-5, the separator device 10 includes a first end 16 and an opposing second end 18. In between the first end 16 and the second end 18, the separator device 10 includes a fixed length portion 20. The fixed length portion 20 has a length L of a known predetermined value. The fixed length portion 20 is preferably linear. The length L of the fixed length portion 20 may be from 5 mm to 1000 mm, more preferably 200 mm to 800 mm, more preferably 400 mm to 700 mm, and more preferably 450 mm to 650 mm. In one example embodiment the length L is about 600 mm. As best seen in FIG. 4, one end of the fixed length portion 20 abuts against an end of the support platform 8, while the other end of the fixed length portion 20 (which is also the second end 18 of the separator device 10) may include a guide adapter 22. In other words, the second end 18 of the separator device 10, which is also the end of the fixed length portion 20, includes a guide adapter 22. The guide adapter 22 is configured to mate with the medical tube adapter 12 and guides the medical device 3 as it is inserted into the medical tube 14.

As best shown in FIG. 5, the first end 16 of the separator device 10 may be coupled with an end of the support platform 8. In the example embodiment shown in the figures, the separator device 10 includes a coupling member 24 having a "U" shape sized to mate with a lip 26 of the support platform 8. The separator device 10 may thus be coupled with the end of the support platform 8 by sliding the cavity defined by the U-shaped coupling member 24 over the lip 26 of the support platform 8. In other words, the lip 26 of the support platform 8 may be fitted inside the cavity defined by the U-shaped coupling member 24. The size of the coupling member 24 and the rigidity of the material of the guide member 10 may be selected such that the lip 26 of the support platform is held in a tight press-fit manner within the coupling member 24. As also shown in FIG. 5, the separator member 10 may include arm 28 extending from the coupling member 24 that abuts against an underside surface 30 of the support platform 8 to assist in the secure coupling of the guide member 10 to the support platform 8. Other coupling mechanisms may be implemented in place of the U-shaped coupling member 24 and arm 28. For example, an end of the fixed length portion 20 may directly abut against the lip 26 of the support platform 8 via magnetism/ electromagnetism. Other connection options may include hoop and look, snap fit, press fit, threaded thumb screw with threaded holes in both the separator member and support platform, and a threaded hole in one of the separator member and support member along with a threaded post.

Figure 6A:
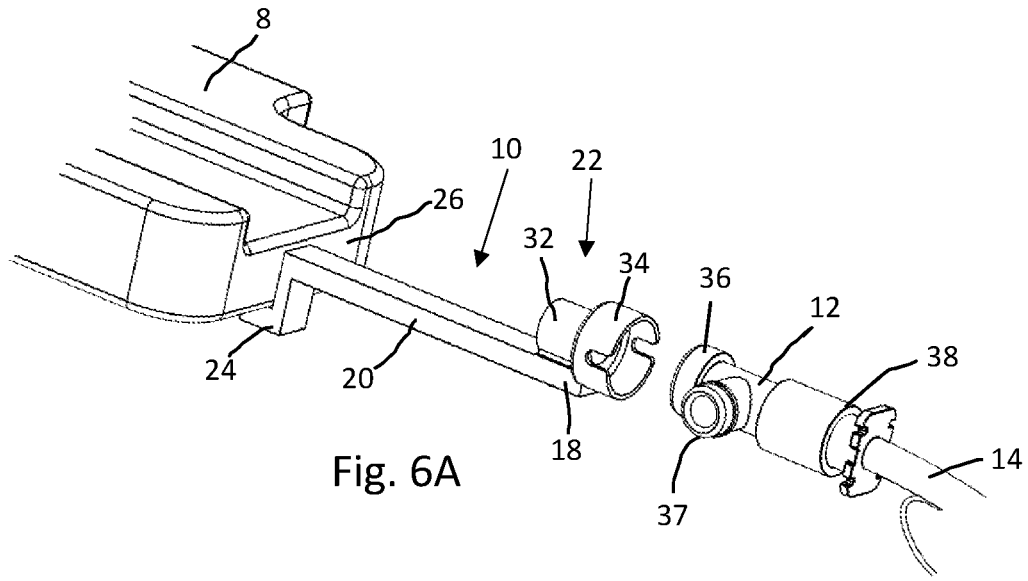
FIG. 6A shows a partial perspective view of the first example embodiment of FIG. 2, in which the guide adapter is not mated with the medical tube adapter.
Figure 6B:
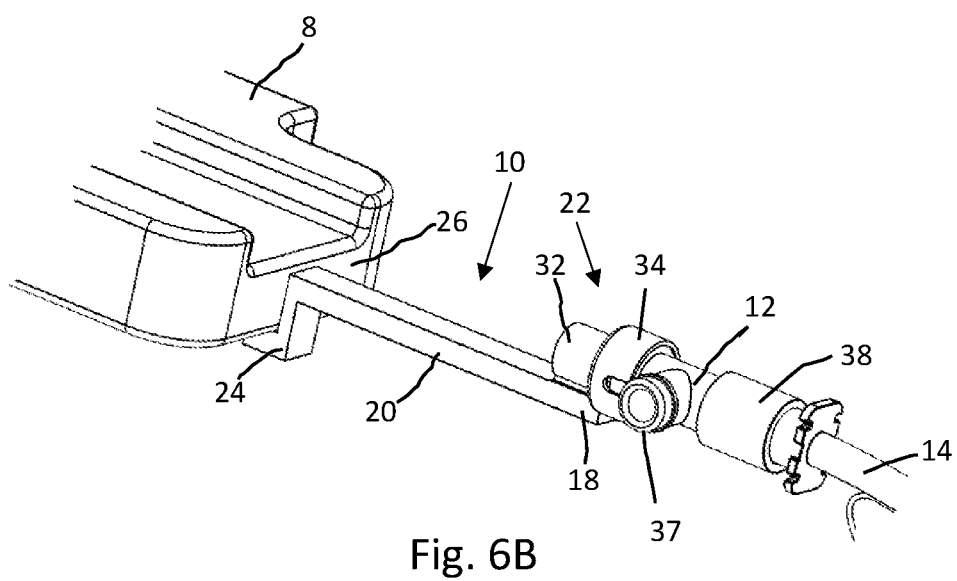
FIG. 6B shows a partial perspective view of the first example embodiment of FIG. 2, in which the guide adapter is mated with the medical tube adapter.

As noted above, the second end 18 of the separator device 10 includes the guide adapter 22. As best shown in FIGS. 6A and 6B, the guide adapter 22 mates with the medical tube adapter 12. FIG. 6A shows a partial perspective view of the first embodiment in which the guide adapter 22 is not mated with the medical tube adapter 12. FIG. 6B shows a partial perspective view of the first embodiment in which the guide adapter 22 is mated with the medical tube adapter 12. As shown in FIGS. 6A and 6B, the guide adapter 22 may have a first portion 32 having a cylindrical shape and a second portion 34 also having a cylindrical shape. The first portion 32 is integrally attached to a surface of the fixed length portion 20 and may have an inner diameter that is equal to or substantially equal to the inner diameter of the medical tube adapter 12. The second portion 34 extends from the first portion 32 and has an inner diameter that is much larger than the inner diameter of the first portion 32 and slightly larger than the outer diameter of a first end 36 the medical tube adapter 12. For example the ratio of the inner diameter of the second portion 34 to the inner diameter of the first portion 32 may be from 2:1 to 1.5:1, while the ratio of the inner diameter of the second portion 34 to the outer diameter of the first end 36 of the medical tube adapter 12 may be 1.05:1 to 1.1:1. The medical tube adapter 12 further includes a ventilator port 37.

Figure 7:
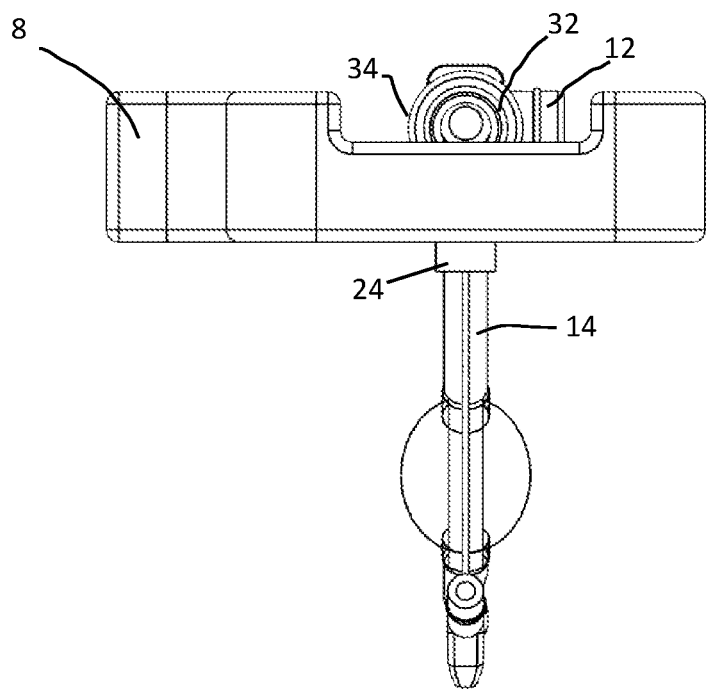
FIG. 7 is a front view of the first example embodiment of FIG. 2, where the viewpoint shows the passageway for a medical device to be inserted.

As shown in FIG. 6B, as a result of the relative diameter sizes, the second portion 34 of the guide adapter 22 is able to mate with the first end 36 of the medical tube adapter 12. That is, as shown in FIG. 6B, the first end 36 of the medical tube adapter 12 is able to fit within the second portion 34 of the guide adapter 22. More particularly, the outer diameter of the first end 36 of the medical tube adapter 12 fits closely within the inner diameter of the second portion 34 of the guide adapter 22. Thus, the first end 36 of the medical tube adapter 12 may be press fit within the second portion 34 of the guide adapter 22. Once connected, a pathway is established from the first portion 32 of the guide adapter 22, to the second portion 34 of the guide adapter 22, and through the medical tube adapter 12. FIG. 7 best illustrates this pathway. FIG. 7 is a front view of the first embodiment of FIG. 2, where the viewpoint shows the alignment of the first portion 32 of the guide adapter 22, the second portion 34 of the guide adapter 22, and the medical tube adapter 12 to define a passageway once mated.

As best seen in FIGS. 2 to 6B, the medical tube adapter 12 has a second end 38 opposite the first end 36 that is mateable with the medical tube 14. In particular, the medical tube 14 has a coupling portion 40 (FIG. 3) having an inner diameter that is slightly smaller than the inner diameter of the second end 38 of the medical tube adapter 12. The coupling portion 40 of the medical tube 14 can thus be inserted into the second end 38 of the of the medical tube adapter 12. When the medical tube 12 mated with the medical tube adapter 12 at the second end 38 and the guide adapter 22 mated with the medical tube adapter 12 at the first end 36, a continuous pathway is established from the first portion 34 of the guide adapter 22 all the way through the medical tube 14.

Because the separator device 10 includes the fixed length portion 20, having a predetermined length, the distance L between the end of the support platform 8 (i.e., the lip 26) and the entrance point of the medical device adapter 12 is known prior to the insertion the medical device 3. In other words, because the length L is known, once the guide adapter 22 is mated with the medical tube adapter 12, the distance between the end of the support platform 8 and the first end 36 of the medical tube adapter 12 is known. This information is used as part of the medical procedure as discussed below.

Figure 8:
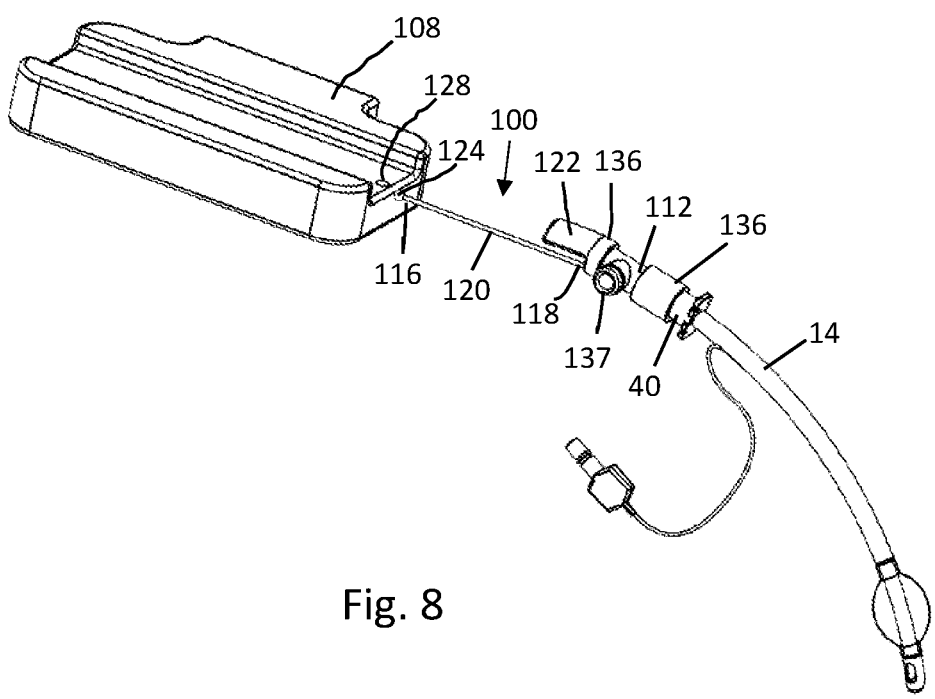
FIG. 8 shows a perspective view of a portion of the medical system in accordance with a second example embodiment, where a support platform, a separator device, a medical tube adapter, and a medical tube are shown.
Figure 9:
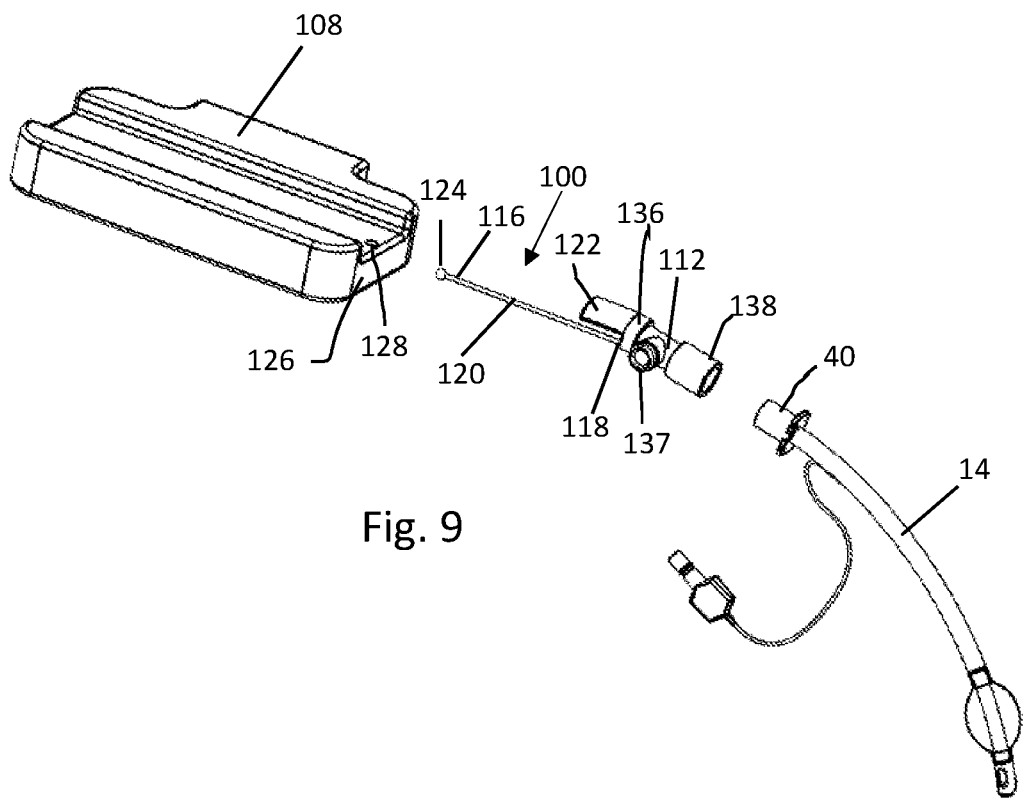
FIG. 9 shows an exploded perspective view of the second example embodiment of FIG. 8.
Figure 10:
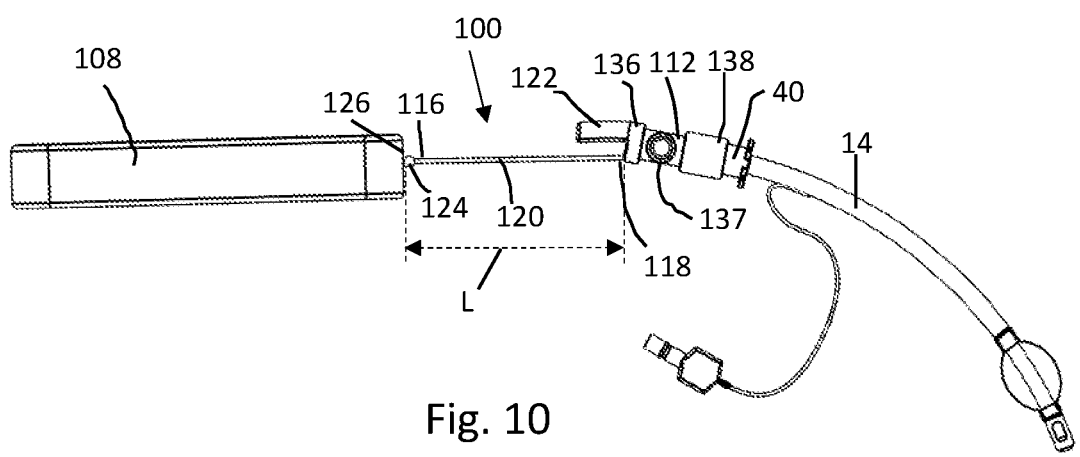
FIG. 10 shows a side view of the second example embodiment of FIG. 8.

FIGS. 8-12, 14A and 14B illustrate a second embodiment. FIG. 8 shows a perspective view of a portion of the medical system in accordance with the second example embodiment, where a support platform 108, a separator device 100, a medical tube adapter 112, and a medical tube 14 are shown. In the second embodiment, the medical tube 14 is identical to the medical tube in the first embodiment. However, as discussed below, the support platform 108, the separator device 100, and the medical tube adapter 112 are different in the second embodiment. FIG. 9 shows an exploded perspective view of second example embodiment of FIG. 8. FIG. 10 shows a side view of second example embodiment of FIG. 8.

The support platform 108 is generally the same as the support platform of the first embodiment and moveably supports the driving unit 2 and medical device 3 in the same manner discussed above. The support platform 108 is different from the first embodiment in that it includes an alignment indicator 128. The alignment indicator 128 may be a marker located on a surface of the support platform 108 adjacent the end 126, as shown. The alignment indicator 128 may be located at the midpoint between the opposing lateral sides of the support platform 108. The use of the alignment indicator 128 is discussed below.

As shown in FIGS. 8-10, the separator device 100 includes a first end 116 and an opposing second end 118. In between the first end 116 and the second end 118, the separator device 100 includes a fixed length portion 120. More particularly, in second example embodiment, the entire length of the separator device 100 is the fixed length portion 120. The fixed length portion 120 has a length L of a known predetermined value. The fixed length portion 120 is preferably linear. The length L of the fixed length portion 120 may be the same as the length L of the fixed length portion 20 in the first embodiment. As best seen in FIG. 10, one end of the fixed length portion 120 (which is also the first end 116 of the separator device Dm) abuts against an end of the support platform 108 in an aligned position, while the other end of the fixed length portion 120 (which is also the second end 118 of the separator device Dm) may be attached to the medical tube adapter 112. That is, the second end 118 of the separator device 100, which is also the end of the fixed length portion 120, is attached to the medical tube adapter 112.

Figure 11A:
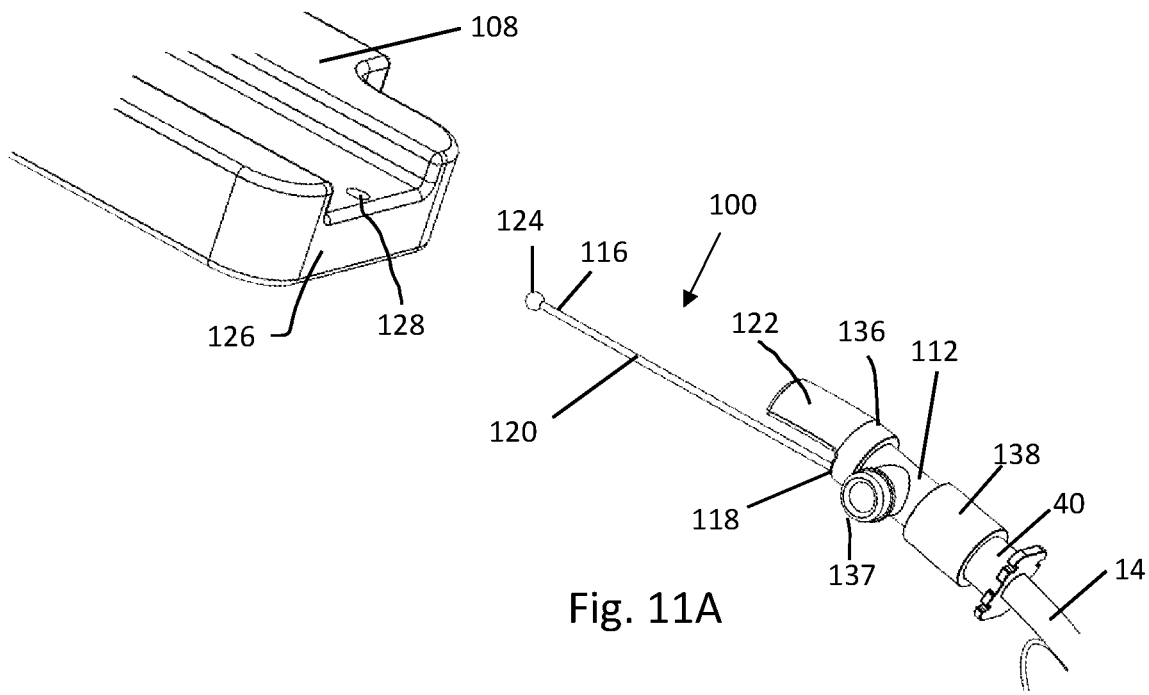
FIG. 11A shows a partial perspective view of the second example embodiment of FIG. 8, in which the separator device is not abutting the end of the support platform.
Figure 11B:
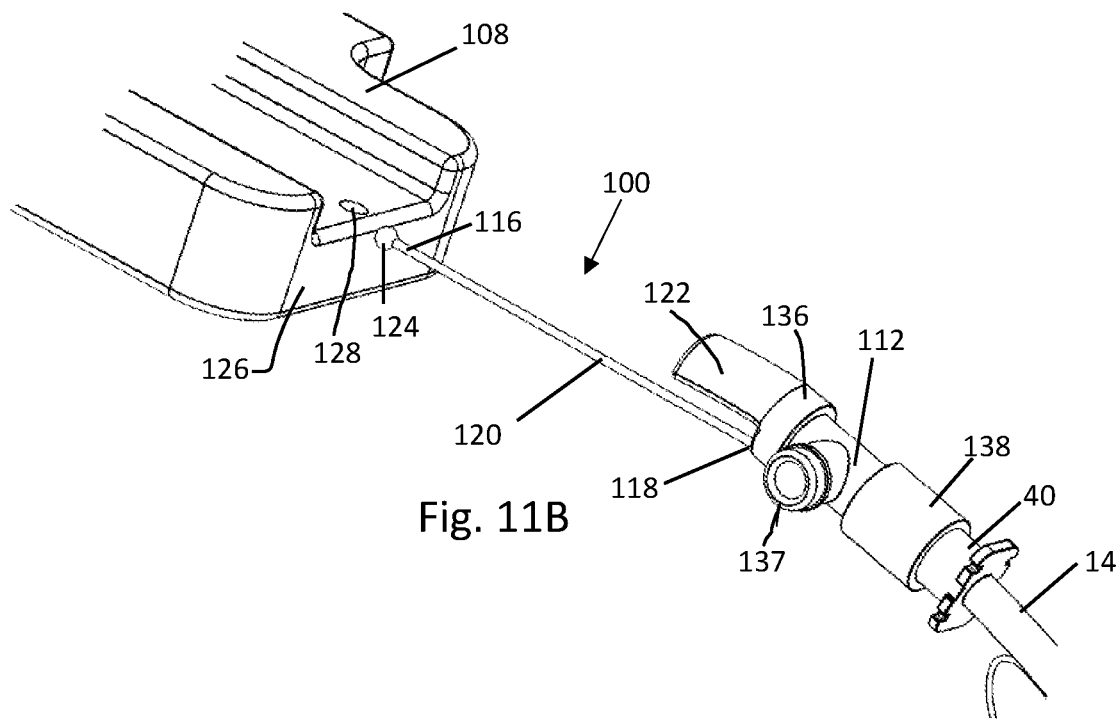
FIG. 11B shows a partial perspective view of the second example embodiment of FIG. 8, in which the separator device is abutting the end of the support platform.

FIG. 11A shows a partial perspective view of the second embodiment in which the separator device 100 is not abutting the end 126 of the support platform 108, i.e., in an unaligned position. FIG. 11B shows a partial perspective view of the second embodiment in which the separator device 100 is abutting the end 126 of the support platform 108, i.e., in an aligned position. As shown in FIGS. 11A and 11B, the first end 116 of the separator device 100 may include an enlarged portion 124. The enlarged portion 124 may be in the shape of a ball tip, as shown. The enlarged portion 128 of the separator device 100 may have a diameter/width several times larger than the diameter/width of the main body of the separator device 100. For example, the diameter/width of the enlarged portion 128 may be 2, 3, 4, 5 or more times larger than the diameter/width of the main body.

As noted above, the support platform 108 includes an alignment indicator 128. As part of performing the medical procedure, which is discussed below, the support platform 108 may be positioned such that the enlarged portion 124 of the separator device 100 abuts the end 126 of the support platform at the location of the alignment indicator 128. That is, the support platform 108 may be moved from a position shown in FIG. 11A (or any other location away from the aligned position) to the position shown in FIG. 11B. Because the separator member 100 is attached to the medical device adapter 112, once the support platform 108 is positioned as shown in FIG. 11B, the medical device adapter 112 is positioned at the known length L from the end 126 of the support platform 108.

Figure 12:
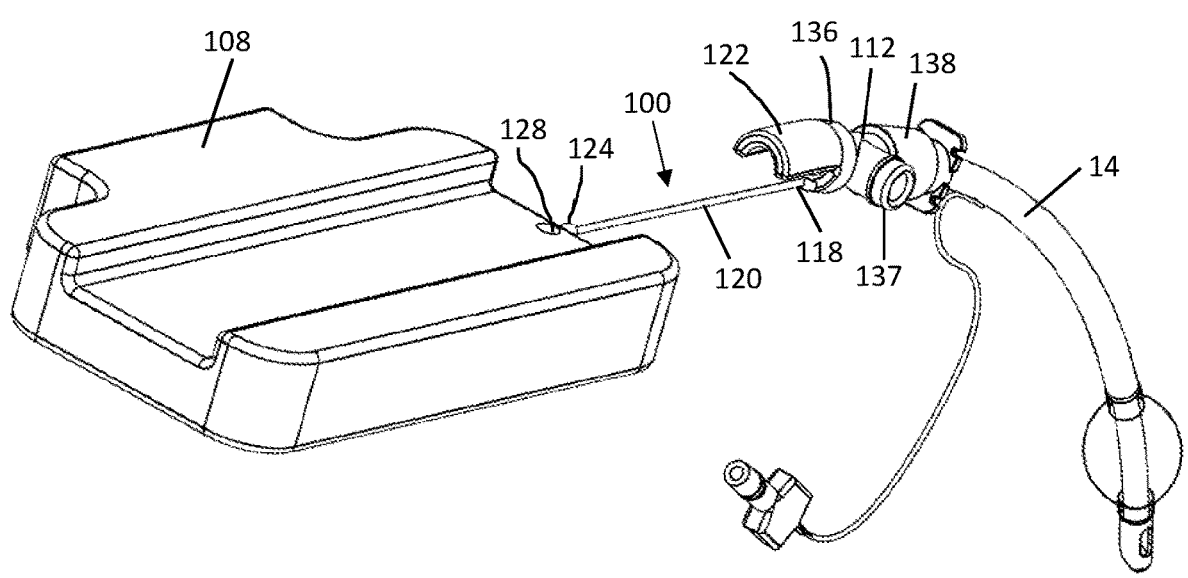
FIG. 12 shows another perspective view of the second example embodiment of FIG. 8.

In the second embodiment, unlike the first embodiment, the separator device 100 does not include a guide adapter at the second end 118. Rather, as noted above, the separator device 100 directly attaches to a first end 136 of the medical tube adapter 112. Therefore, in order to guide the medical device 3, the medical tube adapter 112 in the second embodiment includes a medical device guide 122. The medical device guide 122 extends from the first end 136. FIG. 12 shows another perspective view of the second embodiment. As best seen in FIG. 12, the medical device guide 122 has a semicircle cross sectional shape. Furthermore, as best seen in FIGS. 10-12, the medical device guide 122 extends over the separator device 100. As best seen in FIG. 10, the medical device guide 122 may be curved relative to a longitudinal centerline of the medical tube adapter 112. More particularly, the medical device guide 122 may be curved toward the separator device 100. The curvature of the medical device guide 122 provides a gradual direction change pathway for the medical device 3 to follow.

As best seen in FIGS. 8 to 11B, the medical tube adapter 112 has a second end 138 opposite the first end 136 that is mateable with the medical tube 14 in the same manner as in the first embodiment. The medical tube 14 with coupling portion 40 (FIG. 9) is the same as in the first embodiment including having the same inner diameter. Furthered, the second end 138 of the medical tube adapter 112 is the same as the second end of the medical tube adapter in the first embodiment including having the same inner diameter. Thus, the medical tube 14 mates with the medical tube adapter 112 in the same manner as described in the first embodiment. The medical tube adapter 112 includes a ventilator port 137 similar to the medical adapter tube of the first embodiment.

Because the separator device 100 includes the fixed length portion 120, having a predetermined length, the distance L between the end 126 of the support platform 108 and the first end 136 of the medical tube adapter 112 is known prior to the insertion the medical device 3. In other words, because the length L is known, once the support platform 108 abuts the enlarged portion 124 at the alignment indicator 128, the distance between the end of the support platform 108 and the first end 136 of the medical tube adapter 112 is known. This information is used as part of the medical procedure as discussed below.

A medical procedure may be performed using the medical system of the first embodiment or the second embodiment. In the case of the first example embodiment, the method may begin with attaching the separator device 10 to the support platform 8. This can be performed by placing the coupling member 24 around the lip 26 of the support platform 8. As noted above, the separator device 10 may stay coupled with the support platform 8 via a press fit, for example, among other options. However, at this point in the process, the second portion 34 of the guide adapter 22 of the separator device 10 has not yet been mated with the first end 36 of the medical tube adapter 112. This is the configuration shown in FIG. 6A.

Figure 13A:
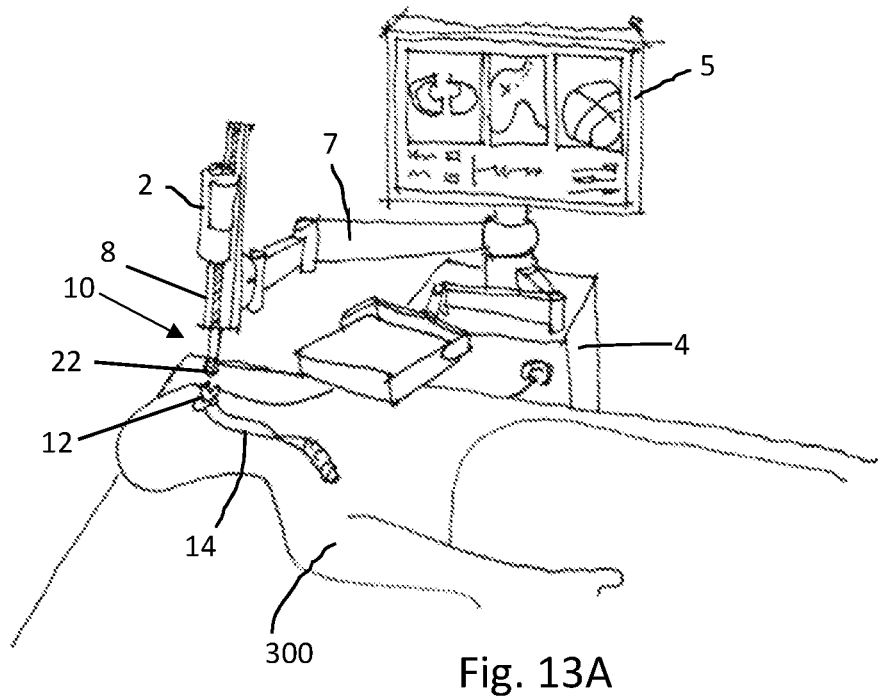
FIG. 13A shows a perspective view of the separator device in the configuration of FIG. 6A when used in conjunction with a patient.

The same configuration of FIG. 6A is shown in FIG. 13A. FIG. 13A shows a perspective view of a first configuration of the separator device 10 of the first example embodiment of FIG. 2 when used in conjunction with a patient 300. That is, FIG. 13A similarly shows the configuration after the separator device 10 has been coupled with the support platform 8, but before second portion 34 of the guide adapter 22 of the separator device 10 has been mated with the first end 36 of the medical tube adapter 12. As shown in FIG. 13A, as this moment in the procedure, the medical tube 14 (e.g., an endotracheal tube) is already inserted into the airway of the patient 300, with the medical tube adapter 12 protruding from the mouth of the patient 300. Next, the operator may move the support platform 8 until the second end 34 of the guide adapter 22 of separator device 10 is mated with the first end 36 of the medical tube adapter 12. This is the configuration shown in FIG. 6B.

Figure 13B:
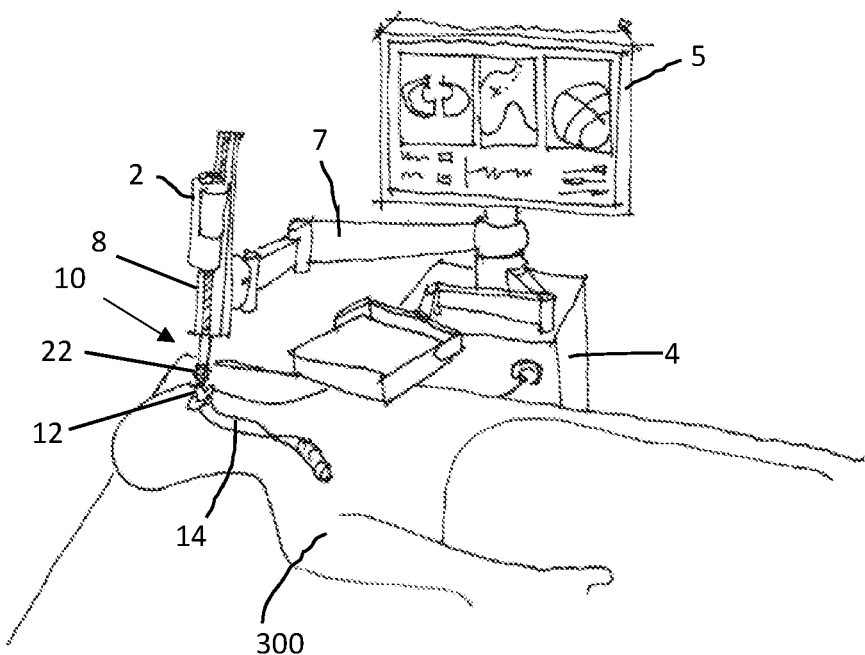
FIG. 13B shows a perspective view of the separator device in the configuration of FIG. 6B when used in conjunction with a patient.

The same configuration of FIG. 6B is shown in FIG. 13B. FIG. 13B shows a perspective view of a second configuration of the separator device 10 of the first example embodiment of FIG. 2 when used in conjunction with a patient 300. FIG. 13B shows the configuration after the second portion 34 of the guide adapter 22 of the separator device 10 has been mated with the first end 36 of the medical tube adaptor 12.

After completing the above steps to arrive at the configuration shown in FIG. 6B and FIG. 13B, the process of inserting a medical device 3 into the medical tube 14 can begin. Because the separator device 10 has the fixed length portion 20, the distance between the end of the support platform 8 and the entrance to the medical tube adapter 12 is precisely known. That is, as best shown in FIG. 4, at this moment in the process, the distance between the end of the support platform 8 and the first end 36 of the medical tube adapter 12 can be precisely known because the length L is known. Furthermore, in the configuration shown in FIG. 6B and FIG. 13B, because the support platform 8 and the pathway of the medical device adapter 12 are in a straight line, the chance of the medical device kinking is greatly reduced.

Figure 14A:
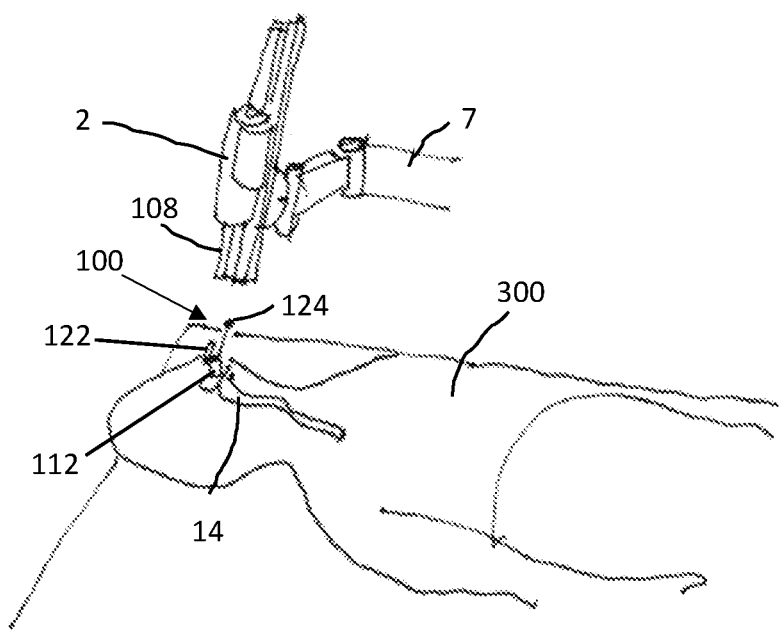
FIG. 14A shows a perspective view of the separator device in the configuration of FIG. 11A when used in conjunction with a patient.

In the case of the second embodiment, the method may begin with aligning the separator device 100 to the support platform 108. The configuration prior to the alignment is shown in FIG. 11A, i.e., where the support platform 108 is not abutting the enlarged portion 124 of the operator device 100. The same configuration of FIG. 11A is shown in FIG. 14A. FIG. 14A shows a perspective view of a first configuration of the separator device 100 of the second example embodiment of FIG. 8 when used in conjunction with a patient 300, with the position cart 4 and the operation console 5 being omitted. FIG. 14A shows the configuration before the support platform 108 has been moved such that the separator device 100 abuts the support platform 108. As shown in FIG. 14A, as this moment in the procedure, the medical tube 14 is already inserted into the airway of the patient 300, with the medical tube adapter 112 protruding from the mouth of the patient 300.

The alignment can be performed by aligning the alignment indicator 128 of the support platform 108 with the enlarged portion 124 of the separator device 100. More particularly, the support platform 108 may be moved until the end 126 of the support platform adjacent the alignment indicator 128 abuts the enlarged portion 124 of the separator device 100. This is the configuration shown in FIG. 6B.

Figure 14B:
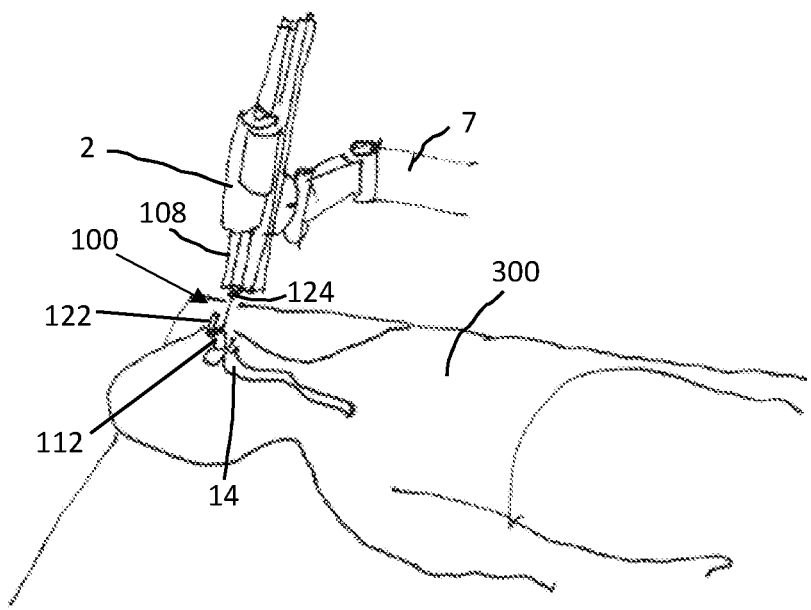
FIG. 14B shows a perspective view of the separator device in the configuration of FIG. 11B when used in conjunction with a patient.

The same configuration of FIG. 6B is shown in FIG. 14B. FIG. 14B shows a perspective view of a second configuration of the separator device 100 of the second example embodiment of FIG. 8 when used in conjunction with a patient 300. FIG. 14B shows the configuration after the support platform 108 has been moved such that the separator device 100 abuts the support platform 108.

After completing the above steps to arrive at the configuration shown in FIGS. 6B and 11B, the process of inserting a medical device 3 into the medical tube 14 can begin. Because the separator device 100 has the fixed length portion 120, the distance between the end of the support platform 108 and the entrance to the medical tube adapter 112 is precisely known. That is, as best shown in FIG. 10, at this moment in the process, the distance between the end 126 of the support platform 108 and the first end 136 of the medical tube adapter 112 can be precisely known because the length L is known. Furthermore, in the configuration shown in FIGS. 6B and 11B, because the medical tube adapter 112 includes the curved medical device guide 122, there is a gradual direction change pathway for the medical device to follow. Thus, the chancing of kinking during insertion is reduced.

The above steps may be considered the preparation steps prior to performing the active portion of the procedure. That is, the steps of arriving at the aligned arrangement occur prior to the operator inserting medical device 3 into the medical tube 14. The process of using the medical system 1 to perform the rest of the procedure may be the same as a typical process using a computer to assist in reaching a target location in the lungs of a patient. For example, after the alignment step is complete, the operator may manually insert the medical device 3 through the medical tube adapter 12, 112 continuing through the trachea until reaching the carina. Once the medical device 3 has reached the carina through manual insertion the method may switch to robot assistance. Once the robot assistance is activated, the operator may use a joystick or other controller at the operation console 5 to instruct the driving unit 2 to advance the medical device 3. The joystick/controller may also be remote from the operation console while maintaining communication with the computer. Other types of motion such as rotation and angling of the tip of the medical device 3 can similarly be achieved through robot assistance.

When the operator is attempting to reach a target location in lungs of the patient, for example to reach a lesion location that has been previously identified using imaging, in order to know the location of the tip of the medical device 3 relative to the target location at any given moment, it is necessary to know precisely how far the support platform 8, 108 is from the medical tube adapter 12, 112. Using the separator device 10, 100 allows the navigation software to already have that information. For example the length L discussed above may be preprogrammed into the computer such that the operator does not need to provide the information. In other embodiments, the length L may be larger or smaller depending on operator preference, room size, and other factors. The software may be programmed to automatically identify which length separator is being used in the particular procedure or the software may have the operator manually indicate which length separator is being used.

With the length L known to the software, when the operator instructs the system to move the medical device 3 to a certain location, the software is able to determine how much to advance the medical device 3 via the driving unit 2 to advance toward, and eventually arrive at, the target location. Without the distance between the end of the support platform 8, 108 and the medical tube adapter 12, 122 being known, it would not be possible for the system to make this determination. By using the separator device 10, 100, the system is able to know the distance information without complex sensors and/or trackers. In other words, by setting the distance L via the separator device 10, 100, the operator has removed a variable from the process.

The system 1 may be regulated, controlled, and/or directed by one or more processors (controller) in communication with one or more components and/or subsystems of the overall system 1. The processor may operate based on instructions in a computer readable program stored in a non-transitory computer readable memory. The processor may be or include one or more of a CPU, MPU, GPU, ASIC, FPGA, DSP, and a general purpose computer. The processor may be a purpose built controller or may be a general purpose computing device that is adapted to be a controller. Examples of a non-transitory computer readable memory include but are not limited to RAM, ROM, CD, DVD, Blu-Ray, hard drive, networked attached storage (NAS), an intranet connected non-transitory computer readable storage device, and an internet connected non-transitory computer readable storage device.

The invention claimed is:

1. A medical system comprising:
an operation console;
a support platform configured to support a catheter;
a driver including an actuator and a control circuit, the driver being moveably coupled to the support platform and being configured to advance or retract the catheter based on an instruction from the operation console;
a separator device couplable with the support platform, the separator device including:
a first end;
a second end opposite the first end;
a guide adapter at the second end; and
a fixed length rod portion between the first end and the second end that extends from the guide adapter; and
a medical tube adaptor including:
a first end;
a second end opposite the first end and mateable with a medical tube; and
a ventilator port between the first end of the medical tube adapter and the second end of the medical tube adapter, the medical tube being insertable into a mouth of a patient,
wherein the guide adapter is attached to or configured to mate with the first end of the medical tube adapter such that the second end of the separator device is closer to the ventilator port than the first end of the separator device and such that the catheter passes through the guide adapter external to the fixed length rod portion.

2. The medical system of claim 1, wherein the guide adapter includes:
a first portion attached to the second end of the separator device; and
a second portion that extends from the first portion,
wherein the second portion is mateable with the first end of the medical tube adapter.

3. The medical system of claim 2, wherein the first portion and the second portion each have a cylindrical shape.

4. The apparatus of claim 3, wherein the first portion and the second portion each have a center defining a passageway.

5. The medical system of claim 3, wherein an inner diameter of the first portion is equal to an inner diameter of the medical tube adapter.

6. The medical system of claim 3, wherein an inner diameter of the second portion is larger than an outer diameter of the first end of the medical tube adapter.

7. The medical system of claim 1, wherein the medical tube is an endotracheal tube.

8. The medical system of claim 1, wherein the separator device is couplable with the separator device via a coupling portion of the separator device.

9. The medical system of claim 8, wherein the fixed length rod portion extends from the coupling portion to the second end of the separator device.

10. The medical system of claim 8,
wherein the support platform includes a lip at an end of the support platform, and
wherein the coupling portion is coupleable with the lip of the support platform.

11. The medical system of claim 1, wherein the second end of the separator device is attached to the medical tube adapter.

12. The medical system of claim 11, wherein the first end of the separator device includes an enlarged portion.

13. The medical system of claim 11, wherein the support platform includes an alignment indicator at an end of the support platform.

14. The medical system of claim 11, wherein the fixed length rod portion extends from the first end of the separator device to the second end of the separator device.

15. The medical system of claim 11, wherein the medical tube adapter includes a medical device guide extending from the first end of the medical tube adapter.

16. The medical system of claim 15, wherein the medical device guide is curved.

17. The medical system claim 15, wherein the medical device guide extends over the separator device.

18. The medical system of claim 1, further comprising:
a positioning arm coupled with the support platform,
wherein the positioning arm is configured to position the support platform relative to a patient.

19. A method of performing a medical procedure using a medical system including:
an operation console;
a support platform configured to support a catheter;
a driver including an actuator and a control circuit, the driver being moveably coupled to the support platform and configured to advance or retract the catheter based on an instruction from the operation console;
a support platform configured to support the catheter;
a separator device including:
a first end;
a second end opposite the first end;
a guide adapter at the second end; and
a fixed length rod portion between the first end and the second end that extends from the guide adapter; and
a medical tube adaptor including:
a first end;
a second end opposite the first end and mated with a medical tube; and
a ventilator port between the first end of the medical tube adapter and the second end of the medical tube adapter, the medical tube being insertable into a mouth of a patient,
the method comprising:
a) coupling the first end of the separator device to the support platform;
b) mating the second end of the separator device with the first end of the medical tube adapter; and
c) after performing a) and b), actuating the driving unit to advance the catheter into the medical tube via the medical tube adapter such that the catheter passes through the guide adapter external to the fixed length rod portion.

20. The medical system of claim 1,
wherein the medical tube adapter has an inner diameter, and
wherein the second end of the separator device is mateable with or attached to the first end of the medical tube adapter such that the separator device extends from a portion of the medical tube adapter located radially outward of the inner diameter.

21. A medical system comprising:
an operation console;
a support platform configured to support a catheter;
a driver including an actuator and a control circuit, the driver being moveably coupled to the support platform and being configured to advance or retract the catheter based on an instruction from the operation console;

a separator device couplable with the support platform, the separator device including:
  a first end;
  a second end opposite the first end; and
  a guide adapter at the second end; and
  a fixed length rod portion between the first end and the second end that extends from the guide adapter; and
a medical tube adaptor including:
  a first end;
  a second end opposite the first end and mateable with a medical tube; and
  a ventilator port between the first end of the medical tube adapter and the second end of the medical tube adapter, the medical tube being insertable into a mouth of a patient,
wherein the guide adapter is attached to or configured to mate with the first end of the medical tube adapter such that the catheter passes through the guide adapter external to the fixed length rod portion.

* * * * *